United States Patent
Lau et al.

(10) Patent No.: US 10,525,614 B2
(45) Date of Patent: *Jan. 7, 2020

(54) BUILT-IN ANTIMICROBIAL PLASTIC RESINS AND METHODS FOR MAKING THE SAME

(71) Applicant: Nano and Advanced Materials Institute Limited, Hong Kong (HK)

(72) Inventors: Yiu Ting Richard Lau, Hong Kong (HK); Sau Kuen Connie Kwok, Hong Kong (HK); Wenjun Meng, Hong Kong (HK); Sheung Yin Li, Hong Kong (HK); Yueying Chen, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 164 days.

This patent is subject to a terminal disclaimer.

(21) Appl. No.: 15/318,585

(22) PCT Filed: Jan. 8, 2016

(86) PCT No.: PCT/CN2016/070500
§ 371 (c)(1),
(2) Date: Dec. 13, 2016

(87) PCT Pub. No.: WO2016/110271
PCT Pub. Date: Jul. 14, 2016

(65) Prior Publication Data
US 2017/0129139 A1    May 11, 2017

Related U.S. Application Data

(60) Provisional application No. 62/124,973, filed on Jan. 9, 2015.

(51) Int. Cl.
| | |
|---|---|
| B29B 9/10 | (2006.01) |
| B29B 7/38 | (2006.01) |
| B29B 9/06 | (2006.01) |
| B29B 9/12 | (2006.01) |
| B29C 51/02 | (2006.01) |
| A01N 25/10 | (2006.01) |
| C08J 3/22 | (2006.01) |
| B29K 105/00 | (2006.01) |
| B29C 48/00 | (2019.01) |

(52) U.S. Cl.
CPC ............... *B29B 9/10* (2013.01); *A01N 25/10* (2013.01); *B29B 7/38* (2013.01); *B29B 9/06* (2013.01); *B29B 9/12* (2013.01); *B29C 51/02* (2013.01); *C08J 3/22* (2013.01); *C08J 3/226* (2013.01); *B29C 48/00* (2019.02); *B29K 2105/0011* (2013.01); *C08J 2300/22* (2013.01); *C08J 2323/12* (2013.01); *C08J 2323/14* (2013.01); *C08J 2325/08* (2013.01); *C08J 2369/00* (2013.01); *C08J 2451/06* (2013.01)

(58) Field of Classification Search
None
See application file for complete search history.

(56) References Cited

U.S. PATENT DOCUMENTS

| | | | |
|---|---|---|---|
| 8,545,862 | B2 | 10/2013 | Toreki et al. |
| 2012/0321689 | A1 | 12/2012 | Kobayashi |
| 2014/0008324 | A1 | 1/2014 | Appeaning et al. |

FOREIGN PATENT DOCUMENTS

| | | |
|---|---|---|
| CN | 102363661 A | 2/2012 |
| CN | 102391520 A | 3/2012 |
| CN | 102942708 A | 2/2013 |
| DE | 19535729 A1 | 3/1997 |
| EP | 2627202 A1 | 8/2013 |
| GB | 2353283 A | 2/2001 |
| WO | 2005021626 A2 | 3/2005 |
| WO | 2012065610 A1 | 5/2012 |

OTHER PUBLICATIONS

Machine translation of CN102942708A, Feb. 27, 2013, p. 1-5.*
Machine translation of CN102363661A, Feb. 29, 2012, p. 1-4.*
NPL Front. Chem. Eng. China. 2008 2_1 102_108.*
Murray et al. Medical Microbiology, 4th ed.; Mosby St. Louis, 2002.
Chung et al. Acta Pharmacol. Sin. 2004, 25, 932.
Dhanalakshmi et al. Mater. Express 2013, 3, 291.
Chang et al. J. Agric. Food Chem. 2012, 60, 1837.
Kenawy et al. Biomacromolecules 2007, 8, 1359.
Pogodin et al. Biophys. J. 2013, 104, 835.
Sin et al. Polym. J. 2014, 46, 436.
Siedenbiedel et al. Polymers. 2012, 4, 46.

(Continued)

*Primary Examiner* — Robert T Butcher
(74) *Attorney, Agent, or Firm* — Spruson & Ferguson (Hong Kong) Limited

(57) ABSTRACT

A built-in and process-adaptive formulation of antimicrobial commodity thermoplastic resins with mixed compositions comprising of a polymer, a backbone linker, and a non-labile antifouling and biocompatible coupling agent which is melt-processable and enabled to be manufactured into finished products in the form of solid, monolith, tube, composite, fiber, film, sheet and varnish without the prerequisite of biocides or antimicrobial additives is disclosed. The said formulation is adapted to thermoforming and thermal curing processes including but not limited to melt compounding, spinning, extrusion, molding, compression foaming and drawing. The antimicrobial property is attributed to the persistent formation of a non-stick bacteria-repellent tethered layer in which the antifouling component of the said formulation is heterogeneously phase separated and/or surface migrated to the surface after product forming in order to minimize adsorption and/or colonization of bacteria.

13 Claims, 12 Drawing Sheets

(56) References Cited

OTHER PUBLICATIONS

Nile et al. J. Mater. Chem. B. 2014, 2, 4911.
International Search Report and Written Opinion dated Apr. 20, 2016 for PCT Application No. PCT/CN2016/070500.

* cited by examiner

BUILT-IN ANTIMICROBIAL PLASTIC RESINS AND METHODS FOR MAKING THE SAME

CROSS REFERENCE TO RELATED APPLICATION

Pursuant to 35 U.S.C. § 119(e), this is a non-provisional patent application claiming benefit from U.S. provisional patent application Ser. No. 62/124,973 filed on Jan. 9, 2015 and titled "built-in antimicrobial plastic resins, preparation and compositions thereof", and paragraphs 0001-0036 and claims 1-10 and 12-20 of the non-provisional patent application are incorporated herein by reference in its entirety.

FIELD OF THE INVENTION

The present invention relates to antimicrobial plastic resins and the methods for making the same, in particular, relates to built-in, biocide-free and safe-to-use antimicrobial plastic resins and the methods for making the same.

BACKGROUND

Despite the biocidal actions to kill the bacteria after attachment to the substrate through several mechanisms, such as inhibition of the synthesis of the cell wall, the nucleic acid, the protein and finally the distortion of the cellular metabolism (Murray et al. *Medical Microbiology*, 4$^{th}$ ed.; Mosby: St Louis, 2002), there are other more natural microbial prevention strategies that can be applied onto the polymer surfaces. While there might be others, one very good example of demonstration is the inherent antimicrobial property of chitosan, a natural polysaccharide derived from the shrimp (Chung et al. *Acta Pharmacol. Sin.* 2004, 25, 932). The most common antimicrobial products adopt bacteria killing as the strategy through biocidal actions and therefore the bacterial prevention effectiveness heavily depends on the release and replenishment of the leachable biocides that are required to migrate to the surfaces from the inner matrix. The biocides must dissipate off the surface for killing a microbe, leaving behind less antimicrobial effectiveness for future microbial encounters. This means that the microbial protection is perishable and has a fixed shelf life. Furthermore, over extended time, the adsorbed microbes on the substrate will gradually adapt to the surfaces, if the biocidal action is not immediate or if biocides are under-dosed at levels below the minimum inhibitory (MIC) or minimum bactericidal concentrations (MBC). Each bacterial isolate has its specific MIC or MBC. This aids to select biocide-resistant microbes.

WO2005021626 discloses a built-in antimicrobial formulation for acrylic polymers by mixing with several organic antimicrobial additives in articles.

US20140008324 discloses methods for processing plastic substrates, comprising at least one of injection molding, thermoforming, or extruding, having inorganic antimicrobial microparticles within and then using plasma etching which results in the removal of a portion of the substrate surface and thereby exposing material within the substrate.

Photocatalysts, such as ZnO and $TiO_2$, exhibit disinfecting effects against gram-positive and gram-negative bacteria and they work only under UV irradiation (Dhanalakshmi et al. *Mater. Express* 2013, 3, 291).

Others employ electrostatic method by the use of cationic polymers, such as chitosan, a natural polysaccharide. The bactericidal action of chitosan targets at the cell membrane of the bacteria which is negatively charged. The bacteria preferentially adsorb to the polymer surface and the strong adhesion leads to a gradual increase in their cell permeability and eventually intracellular dissolution due to the distortion of the charge distribution of the membrane (Chang et al. *J. Agric. Food Chem.* 2012, 60, 1837). However, this approach is not universal to target at a broad spectrum of bacteria bearing different cell membrane charges; some bacteria can be positively charged.

On the other hand, the lower-molecular weight polymers of chitosan were found to be able to diffuse and permeate through the porous membrane into the cells and form stable complexes with DNA. This subsequently prevents the DNA transcription activities, thus leading to inhibition of the proliferation and even the death of bacteria (Kenawy et al. *Biomacromolecules* 2007, 8, 1359).

Another biocidal approach requires complex nanoscale features and pattern topographies, such as nanopillars, which can be found on the insect wings (Pogodin et al. *Biophys. J.* 2013, 104, 835).

DE196060113 discloses a biocide-free coating free from biocides based on organofunctional silanes and fluoroorganosilanes and/or their hydrolysates and/or condensation products but the invention is limited to coatings which function properly with metal substrates, such as aluminum foil.

All these cater for the development of the new approach via a bacteria-repellent layer to be permanently and stably formed on the surface of a commodity plastic article and to prevent adhesion and accumulation of bacteria. This overcomes all the drawbacks that come with the conventional surface coating and/or combined with biocidal approaches.

One feasible antifouling structure is based on electrostatics via charge-bearing polymers, polyelectrolytes, polysaccharides and polypeptides containing amino, quaternized, carboxylated, sulfonated, phosphate, boronate entities and other metal oxides, complexes and their derivatives, of which the zeta potentials can be finely tuned by pH, counterion and charge valence.

U.S. Pat. No. 8,545,862 discloses an anionic/cationic polyelectrolyte complex, for example, a composition consisting essentially of a derivative or copolymer of poly (acrylic acid) or polystyrene sulfonate, to impart antimicrobial properties to an article.

WO2012065610 discloses a long-lasting antimicrobial coating for fabrics comprising a polymeric quaternary ammonium (quat).

EP2627202 discloses an antimicrobial peptide comprising Brad or an active variant thereof as a food preservative to prevent or inhibit spoilage of a foodstuff by a microorganism.

Just this approach, however, is not versatile enough. It is because some bacteria, plasma proteins and red blood cells carry negative charges on their cell membranes and they are expected to show very similar electrostatic repellent behavior against a substrate surface of the same charge. While other species of bacteria can be positively charged, such as *Stenotrophomonas maltophilia*, this approach is therefore not universal to target at a broad spectrum of bacteria as differentiated by the cell membrane charges.

The second feasible structure of antifouling groups is derived from neutral polymers, such as poly(2-hydroxyethyl methacrylate) (polyHEMA), poly(ethylene glycol) (PEG) and Zwitterionic polymers and a heterogeneous polymer system of mixed charges comprising of cationic and anionic functionalities onto the plastic surface (Sin et al. *Polym. J.* 2014, 46, 436). PolyHEMA shows the repellent properties because of its strong hydrophilicity so that it can displace the deposition of bacteria by a tightly bound hydration layer. Hydrophilic surfaces are apparently helpful to avoid bacterial adhesion. PEG however uses the steric exclusion effect to resist the protein and platelet adsorption. Previous data also suggested that the adherence of the bacteria was determined by the composition and the chemical nature of the pre-adsorbed protein layers coupled with the surface hydrophilicity. Zwitterionic polymers are bioinspired from the Zwitterionic phospholipid structures of the cell membranes which are well-known to be bio-inert. As different from the hydrophilic polymers, the betaine-based Zwitterionic polymers can finely tune the electrostatic interactions with the nearby water molecules and control the non-specific protein adsorption. Siedenbiedel et al. reveal successful examples of applications of Zwitterionic polymers for prevention of bacterial adhesion to the surfaces after chemical modification (Siedenbiedel et al. *Polymers.* 2012, 4, 46).

In the third feasible approach, the antifouling property of the plastic material can be achieved by modifying the chemical group functionality which in turn changes the surface hydrophobity via end termination and/or grafting of a polymer chain with alkyl, hydroxyl, fluoroalkyl and/or aromatic entities (Nie et al. *J. Mater. Chem. B* 2014, 2, 4911), completely different adhesion and physicochemical behaviors of biomolecules onto the surfaces will be acquired.

SUMMARY OF THE INVENTION

Conventional methods of fabrication of antifouling and bacteria-repellent surfaces are achieved mostly by surface chemical grafting, vacuum deposition, in-situ polymerization, spin-coating and dip-coating of related antifouling materials which have low throughputs. Another technical problem with surface modification is the prerequisite of post-treatment, such as thermal curing, photoreactions, etc. in order to ensure a uniform coverage of the coating on the articles whereas the shape limitations with curved, inner lumen and fine features are often encountered for different finished consumer products. While commodity plastic products are mainly manufactured by thermoforming processes, injection molding and extrusion in a large-scale and continuous mode of operation in plastic industries, any add-on surface modification and/or post-treatment processes to the existing production lines are certainly not desirable to manufacturers in consideration of the new capital investment.

The objective of this invention is to develop biocide-free resins overcoming the shortcomings of limitation to surface coatings or leaching out in existing technologies. Neither bactericidal nor bacteriostatic, the biocide-free resins' surface shows built-in bacteria repellent performance rather than killing performance after product forming.

The present invention is related to a reformulated thermoplastic resin with built-in bacteria-repellency and adaptability to thermoforming processes. The nonfouling functionalization of a base polymer is performed by reactive melt extrusion of a commercial thermoplastic resin, such as maleic anhydride bearing polyethylene, with an appropriate antifouling coupling agent comprising of one or more similar bio-repellent structures in the said chemical approaches and/or other free-radical initiators and acid/base catalysts, such as sodium periodate, azobisisobutyronitrile, benzoyl peroxide, dicumyl peroxide, potassium persulfate, p-toluenesulfonic acid, 4-dimethylaminopyridine, stannous chloride, dibutyltin dilaurate and trimethylsilyl chloride, thus leading to a masterbatch resin after cooling and pelletization.

The resin is then molded into finished articles which display antimicrobial performance after a thermoforming process. The incorporated antifouling groups of the invention can phase segregate and inhabit the surfaces during article forming processes, hence introducing permanent barriers against bacterial adhesion via a chemically-stable repellent surface on the neat plastic article. The thermoplastic resin includes but not limited to the family of polyolefin, polyether, polyvinyl, polyester, polyacetal, polyamide, polyurethane, polyacrylate, polycarbonate, polyimide, polyphthalate, polysulfone, polythioether, polyketone, epoxide and other elastomeric polymers, such as silicone, polyisoprene, acrylonitrile butadiene styrene and ethylene vinyl acetate. Because of the low-cost and high-volume production capability using thermoforming processes, typically melt extrusion and injection molding, the formulation is melt-processable and exhibits strong thermal chemical stability up to a temperature as high as 350° C. Moreover, it tends not to interfere with the manufacturer's production line and the physical bulk properties, such as optical transparency, thermal conductivity, mechanical stiffness, electrical conductivity, dielectric strength and flammability rating, of the formed articles comprising of the formulation. The articles can be in the form of composite, fiber, sheet and varnish.

After thermoforming, a non-stick bacteria-repellent layer of polymer brush on the article surface is formed by heterogeneous phase separation, crystalline ordering and/or surface-directed migration of the backbone-grafted antifouling groups of the present invention to minimize the initial physical or chemical adsorption of motile planktonic bacterial cells and later colonization of the harbored cells leading to formation of irreversible biofilms that can withstand host-defense measures or any antibiotics in use. The tethered layer has covalently been tied with the neat matrix after article forming. This provides unperishable protection of the surface from bacterial attachment. The said brush layer is not bactericidal or bacteriostatic. This means that the mechanism of action for microbial prevention is not achieved by killing or growth inhibition of bacteria. No leachable and non-biodegradable biocidal additives are involved to move to the surface to work. This can entirely eliminate the chance to generate biocide-resistant bacteria. The invention is therefore safe-to-use in the way that the antifouling layer is biocompatible, non-cytotoxic and does not lead to neither skin allergies on contact nor persistent bioaccumulation in eco-system.

DETAILED DESCRIPTION OF THE INVENTION

To illustrate the structure and advantages of the present invention, below is the detailed description of the present invention in combination with the figures and embodiments.

The present invention discloses an antimicrobial thermoplastic resin, which comprises a masterbatch and a basic plastic, the masterbatch is prepared by grafting an antifouling reagent onto an intermediate. The intermediate is prepared by grafting a reactive linker onto a base polymer backbone.

The base polymer backbone is a synthetic vinyl polymer with R groups. The R groups are linear and/or multi-armed chemical structures with homo- or hetero-substituted alkyl, alkenyl, alkynl, aryl, acyl, alkoxyl, thionyl, cyano, azo, silyl groups, halogens and/or cyclics. The antifouling reagent is a hydrogel forming polymer, constituting polyol, polyoxyether, polyamine, polycarboxylate, polyacrylate, polyacrylamide, polyvinylpyrrolidone, polysaccharide, Zwitterionic polyelectrolyte, a copolymerized system of polymer segments of mixed charges and/or an interpenetrating blend mixture of cationic and anionic polymers. Preferably, the antifouling reagent is polyethylene glycol. The reactive linker is thermally reactive and applies to ester-, oxo-, imine-, azole-, methine-, urea-, carbonate-, amide-, carbamate-, disulfide-, siloxane-directed or transition metal-based cross-coupling precursors. Preferably, the reactive linker is maleic anhydride. The basic plastic is a thermoplastic and melt-processable plastic resin including polyolefin, polyether, polyvinyl, polyester, polyacetal, polyamide, polyurethane, polyacrylate, polycarbonate, polyimide, polyphthalate, polysulfone, polythioether, polyketone, epoxide and elastomer. The antimicrobial thermoplastic resin may contain non-biocidal additives, including but not limited to catalysts, initiators, stabilizers, foaming agents, plasticizers, thickeners, lubricants, fillers, impact modifiers, antiblocks, clarifiers, antistatics, flame retardants and/or colorants.

Figure 1:
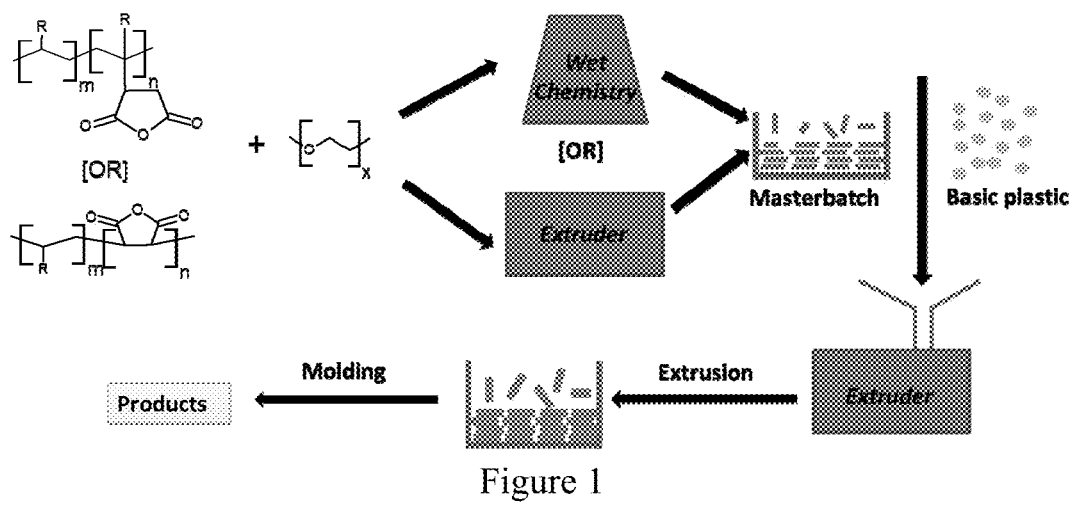
FIG. 1 is a schematic diagram of the preparation process of an embodiment of the present invention.

Referring to FIG. 1, a preparation process of the antimicrobial thermoplastic resin is shown. An intermediate is prepared by grafting a reactive linker on a base polymer backbone. A masterbatch resin is prepared by grafting an antifouling reagent onto the intermediate. The masterbatch resin is melt extruding to prepare a masterbatch and then the masterbatch is dried and pelletized after cooling. Melt compounding the masterbatch and a basic plastic to prepare the antimicrobial thermoplastic resin. Molding into a finished article by a thermoforming process. The thermoforming process includes spinning, extrusion, injection, compression, foaming and drawing. The finished article is molded into a form including solid, monolith, tube, composite, fiber, film, sheet and varnish.

Embodiment 1

In this embodiment, therefore, poly(ethylene glycol) (PEG) was selected as the antifouling reagent to render the modified base polymers' bacterial repelling property. The masterbatches of PEG derivatives were introduced to the commercially available resins: polypropylenes (PP), polyethylenes (PE) and polycarbonates (PC). PP and PE demonstrate low melt processing temperatures while PC demonstrates high melt processing temperature.

1.1 Wet synthesis of PEG-Bearing Styrene-Maleic Anhydride Copolymer (SMA-PEG) as Masterbatch.

SMA-PEG was prepared by grafting PEG 10,000 (Tianjin Kermel) onto the backbone of styrene-maleic anhydride (SMA) copolymer (Sigma-Aldrich, Catalog no. 442399) in acetone. In other words, 100 g of PEG 10,000 was first dissolved in 500 mL of boiling acetone to give a 20 wt % PEG solution. 3.2 g of SMA was subsequently dissolved in the PEG solution and the reaction mixture was stirred under reflux overnight. The reaction was quenched in hexane to give a white precipitate. The powdery precipitate was purified by filtration, followed by vacuum drying at room temperature. Equation 1 illustrates the synthetic route to obtain SMA-PEG.

Equation (1):

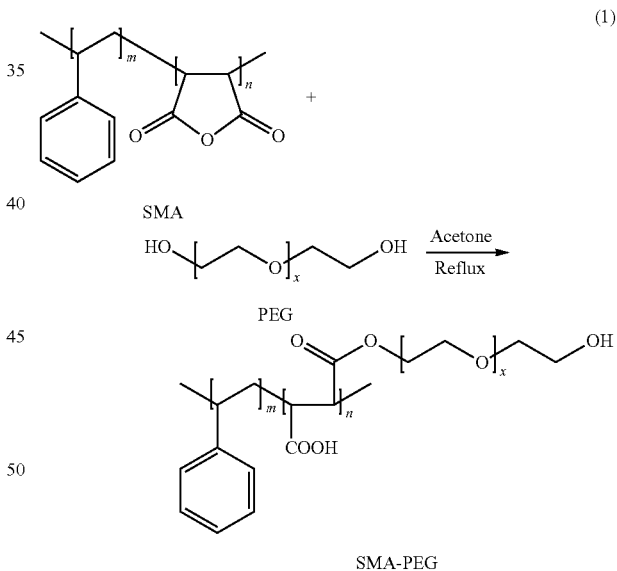

Figure 2:
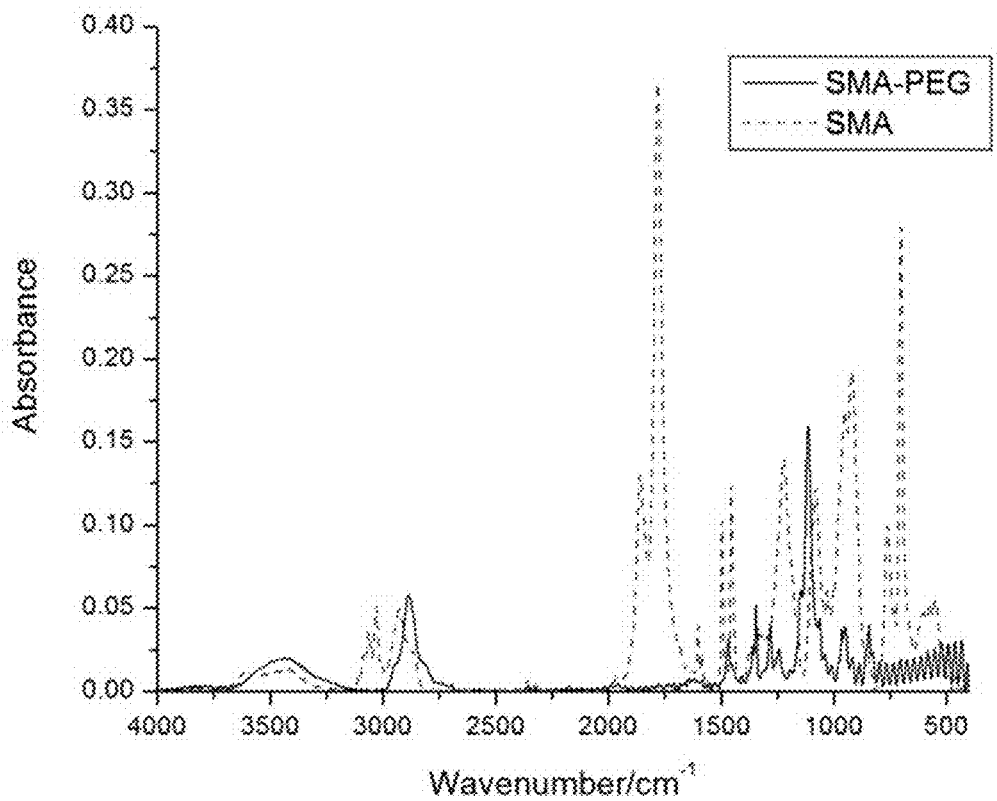
FIG. 2 is an ATR-FTIR spectrum of PEG-bearing styrene-maleic anhydride copolymer (SMA-PEG) and styrene-maleic anhydride copolymer (SMA).

From the attenuated total reflection-Fourier transform infrared (ATR-FTIR, Bruker Vertex 70 Hyperion 1000 with PLATINUM ATR, diamond crystal probe, DLaTGS detector) spectrum of SMA (c.f., dashed line in FIG. 2), the absorption band over 3000 cm$^{-1}$ corresponds to alkenyl C—H and C=C stretching modes of unsaturated aromatics, indicating the presence of styrene units. Another feature is the sharp absorption band from 2000 cm$^{-1}$ to 1600 cm$^{-1}$ which is a unique feature of cyclic anhydride, an indication of maleic anhydride in SMA. These two features are clearly absent in the ATR-FTIR spectrum of SMA-PEG (c.f., solid line in FIG. 2). The disappearance of the characteristic aromatic band (above 3000 cm$^{-1}$) is mainly due to the decrease of the concentration of styrene units of SMA-PEG near the surface because ATR-FTIR is a surface-sensitive characterization technique with a sampling depth of the order of tens of microns. The attenuation of maleic anhydride band indicates the complete consumption of maleic anhydride in SMA by esterification with hydroxyl end group of PEG.

1.2 Preparation of PP/SMA-PEG

PP (GD-150, Maoming Petro-Chemical Shihua Company) in powder form was selected as the base plastic for preparation of antimicrobial PP resins. 95 g of PP and 5 g of SMA-PEG were mixed thoroughly in a rotating drum mixer (Better Pak International YG-1KG). The drum mixing was performed by repeated 10 clockwise and anticlockwise rotations each for 1 minute at a speed of 60 rpm. The powdery mixture was subsequently extruded on a desktop single-screw extruder (Wellzoom C-type). The extruder has a nozzle diameter of 1.75 mm, length-to-diameter ratio of 10:1 and a maximum screw speed of 10 rpm, where the screw is driven by a 240-W motor. In the experiment, the temperature settings were 195° C. at the barrel and 200° C. at the die of the extruder while the speed of the screw was 5 rpm for extrusion. The extrudate in the form of short filaments was cooled down in air and further cryogenically granulated into powders with a swing-type stainless steel three-blade pulverizer (Laifu LFP-2500A).

Figure 3A:
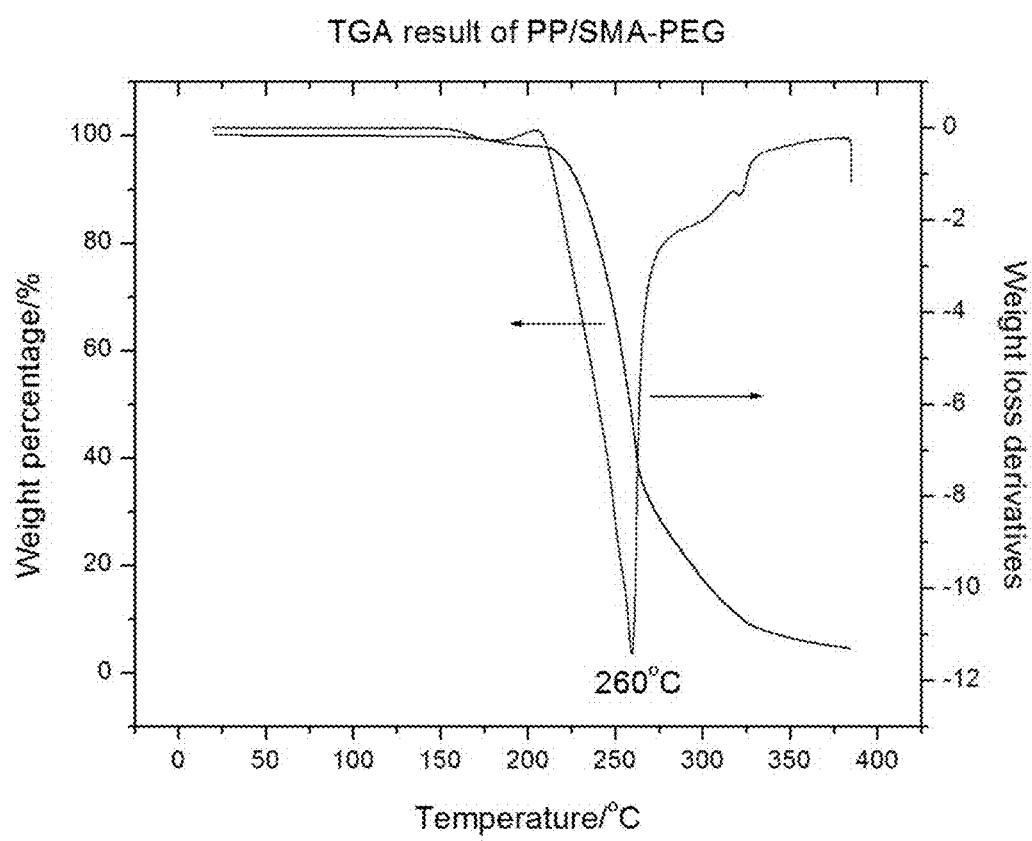
FIG. 3 is a TGA and DSC thermogram of an antimicrobial PP resin (PP/SMA-PEG) using SMA-PEG as masterbatch.

The thermogravimetric (TGA, TA Q5000, at a heating rate of 5° C./min with an air flow rate of 25 mL/min) result (c.f., FIG. 3a) on PP/SMA-PEG sample shows a peak decomposition temperature to be slightly beyond 250° C. alongside a substantial weight loss in air. Certain extent of reduction of the decomposition temperature as compared with the base PP plastic (298° C.) was expected. Although PEG is susceptible to oxidative degradation which worsens upon heating, the TGA result on PP/SMA-PEG has evidently excluded the thermal stability concern with PEG modification.

Figure 3B:
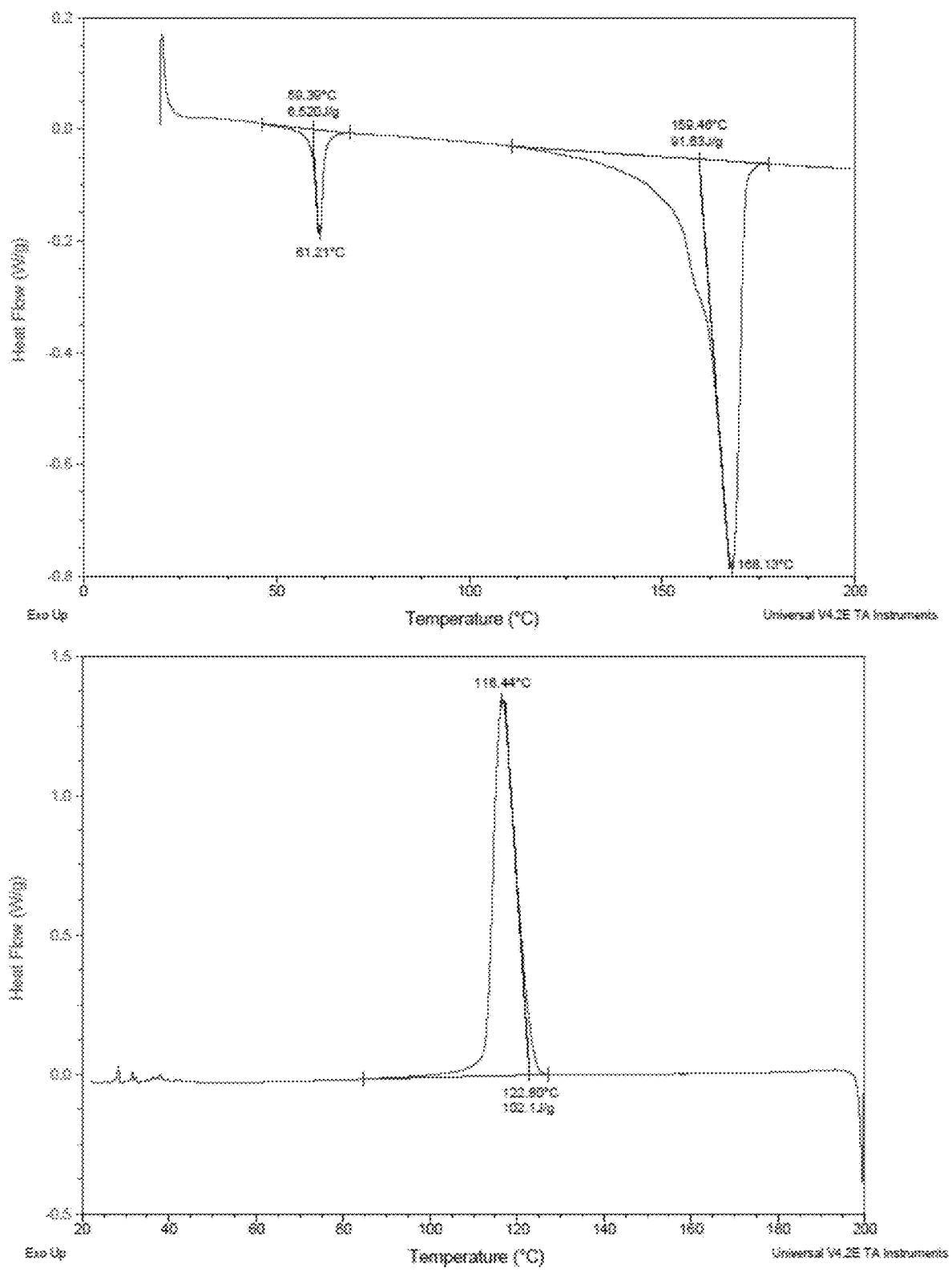

FIG. 3b is shows the differential scanning calorimetry (DSC, TA Q1000) thermograms of PP/SMA-PEG resin in one heating-cooling cycle at a ramping rate of 5° C./min in nitrogen atmosphere. Two endothermic peaks were observed on the heating trace: a peak at 55° C. corresponding to the melting of PEG and a peak at 165° C. corresponding to the melting of PP, thus making it suitable for injection molding or other subsequent thermoforming processes for article formation which fits within the processing window of 30 to 50° C. above its melting temperature. The evolution of the two peaks indicates the formation of phase separated morphology of the as-extruded PP/SMA-PEG resin.

The melt flow index of PP/SMA-PEG was measured on a melt indexer (Model KL-MI-BP, Dongguan Kunlun Testing Instrument Company) to be 13.20 g/10 min at 190° C. under the load of 2.16 kg, a value higher than that of the pristine PP (GD-150) which was 9.68 g/10 min. At 230° C. under the same load, the melt of PP/SMA-PEG resin flowed like water very rapidly.

1.3 Fabrication of Antimicrobial PC Resins (PC/SMA-PEG) Incorporating Antifouling Masterbatch PC/SMA-PEG was prepared by single-screw extrusion of a blend of PC (Teijin Panlite® L1225Y) granules (95 g) and SMA-PEG powders (5 g) which have been pre-mixed in a drum mixer by the same condition. The barrel and the die temperature for extrusion were set at 275° C. and 280° C. respectively. The speed of the screw was adjusted to 3 rpm due to the low melt viscosity of PC. The extrudate in the form of short filaments was cooled down in air and then cryogenically granulated into powders with a three-blade pulverizer.

The melt flow index of the PC/SMA-PEG resin was measured to be 21.60 g/10 min which was nearly double that of the pristine PC (11.68 g/10 min) at 300° C. under the same load of 1.2 kg.

Figure 4A:
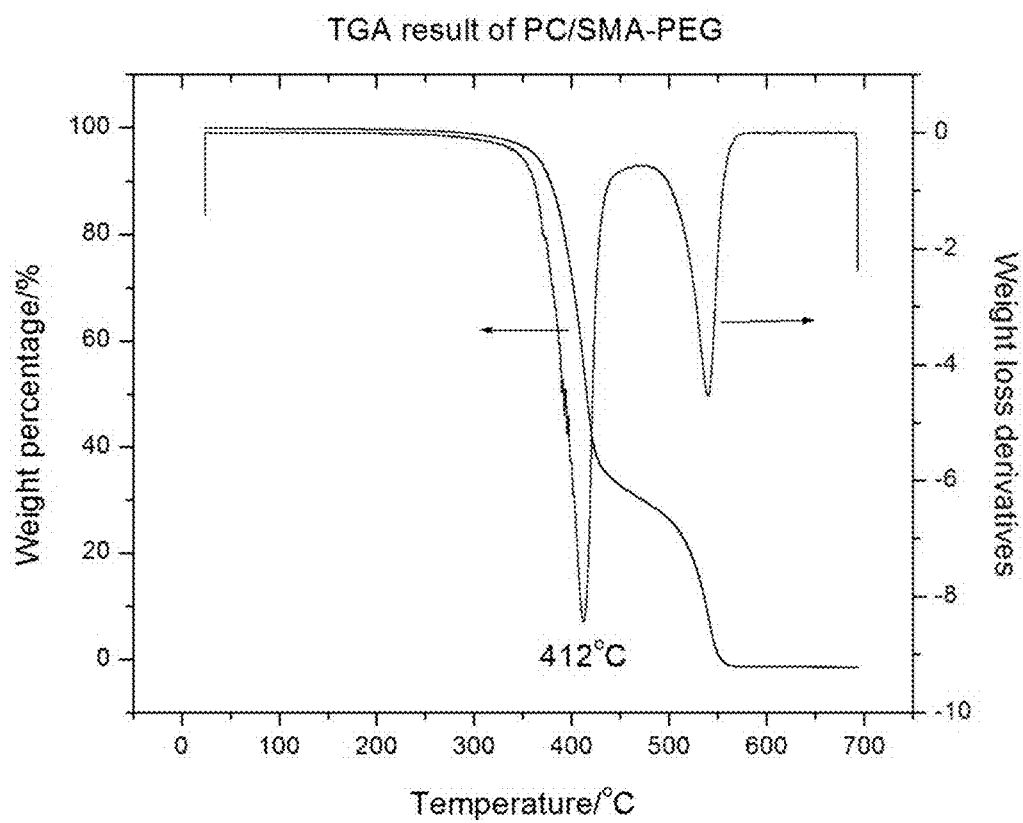
FIG. 4 is a TGA and DSC thermogram of an antimicrobial PC resin (PC/SMA-PEG) using SMA-PEG as masterbatch.
Figure 4B:
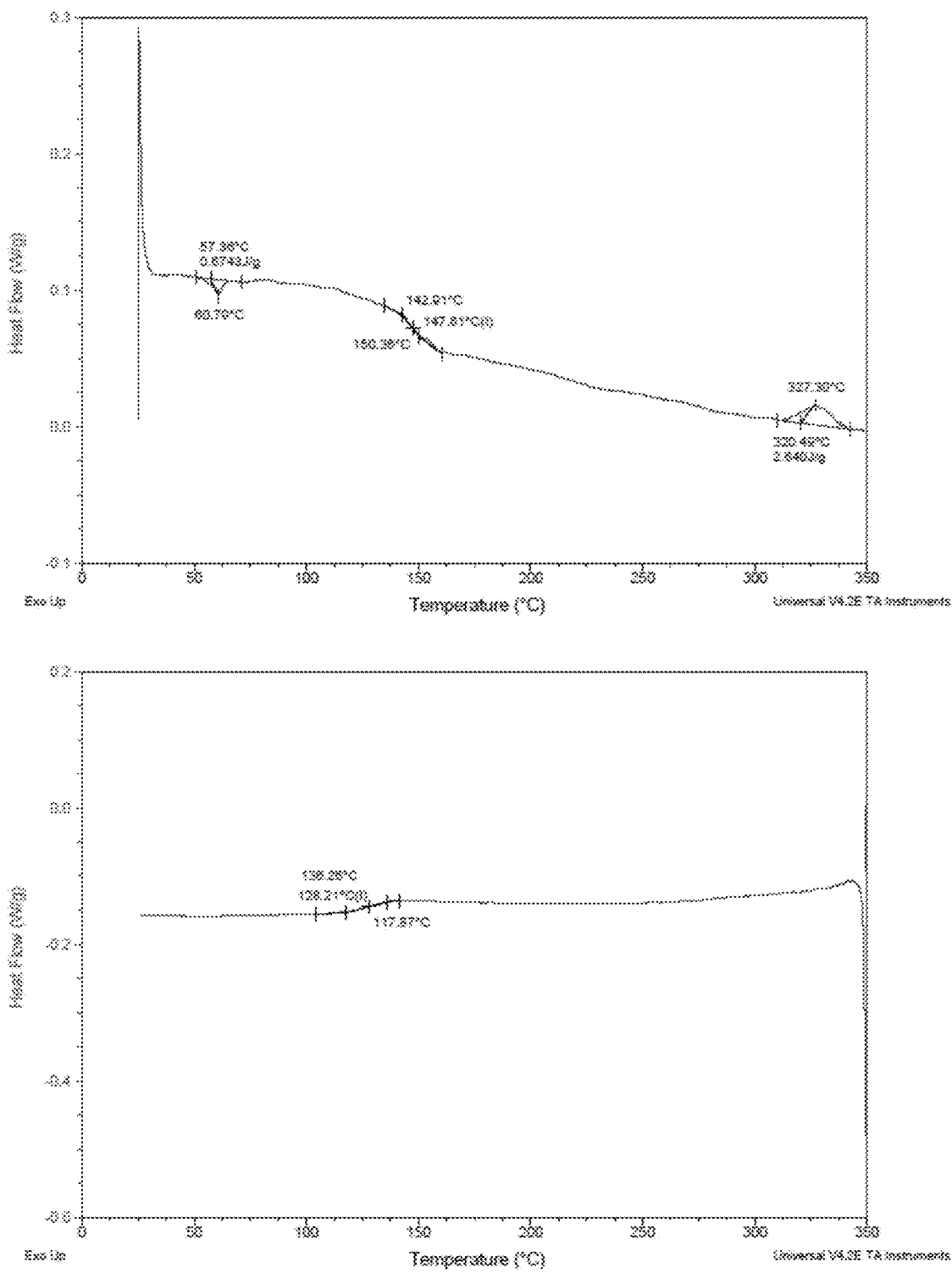

There were two distinct decomposition peak temperatures for the PC/SMA-PEG samples: one near 400° C. and another one near 550° C. (c.f., FIG. 4a). The first decomposition peak might correspond to the decomposition of the resin rich in SMA-PEG content. The first decomposition temperature was not reduced as much compared with the pristine PC which was recorded to be 445° C. Evidence of the presence of SMA-PEG was located on the DSC heating curve of the sample (c.f., FIG. 4b), wherein an endothermic peak was shown at 60° C. This peak is assigned as the melting temperature of SMA-PEG. Since PC is intrinsically an amorphous polymer, no melting peak should be acquired for PC despite the typical second-order endothermic transition at 150° C., which is assigned as the rubber-glass transition temperature of PC. The first-order melting transition observed in PC/SMA-PEG therefore represents the SMA-PEG phase domains in the PC matrix. An additional exotherm is observed at about 327° C. attributing to some extent of bond formation events, most probably transesterification reactions between PC and the free hydroxyl ends of SMA-PEG.

1.4 Fabrication of Antimicrobial PE Resins (PE/SMA-PEG) Incorporating Antifouling Masterbatch PE/SMA-PEG was prepared by twin-screw extrusion of a blend of PE (SABIC® 1922SF) granules (500 g) and SMA-PEG powders (25 g) which have been pre-mixed in a drum mixer by the same condition. The extrusion was undergone on a co-rotating twin-screw extruder (Model AK26, Nanjing KY Chemical Machinery) with a length-to-diameter ratio of 44:1, a screw diameter of 26 mm and a maximum screw speed of 600 rpm. The screw rotation was driven by a 7.5 kW motor. The extruder was connected in line with a water bath followed by a pelletizer. The barrel temperature profile from the front to the rear (with a total of 8 temperature zones) was read as: 150° C., 160° C., 170° C., 170° C., 170° C., 170° C., 170° C., and 160° C. The feed frequency was 2 Hz and the speed of the screw was 150 rpm. The extrudate was solidified from melt upon cooling in water and finally subjected to pelletization. The plastic pellets were then dried in oven at 50° C. overnight.

Embodiment 2

2.1 Wet Synthesis of PEG-Bearing Maleated Polypropylene (PP-MA-PEG) as Masterbatch PP-MA-PEG was prepared by wet chemistry via grafting of PEG 2000 (Tianjin Kermel) onto maleated polypropylene (PP-MA) (Sigma-Aldrich, Catalog no. 427845) with a weight average and number average molecular weight of 9100 and 3900, respectively, under reflux in toluene. 10 g of PP-MA was first dissolved into 200 mL of boiling toluene to give a 5 wt % solution of PP-MA. 20 g of PEG 2000 was added into the PP-MA solution. The reaction mixture was refluxed overnight and quenched in hexane to give product as a white precipitate. The precipitate was filtered to remove unreacted PEG and finally dried at room temperature in vacuum. The reaction scheme is demonstrated in Equation 2.

Equation (2):

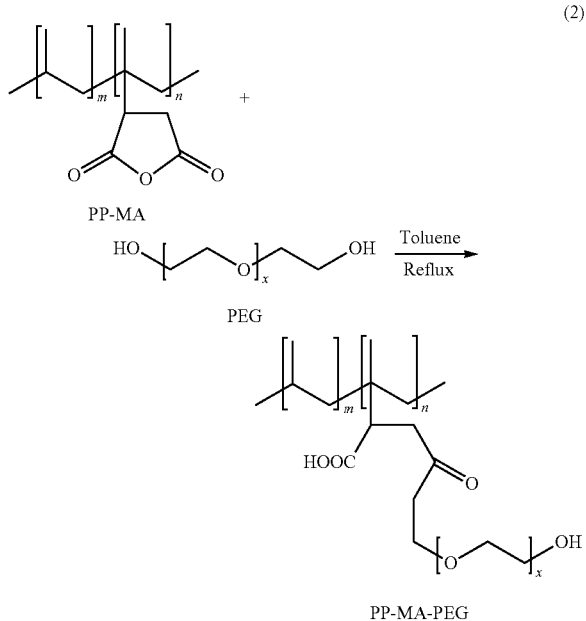

Figure 5:
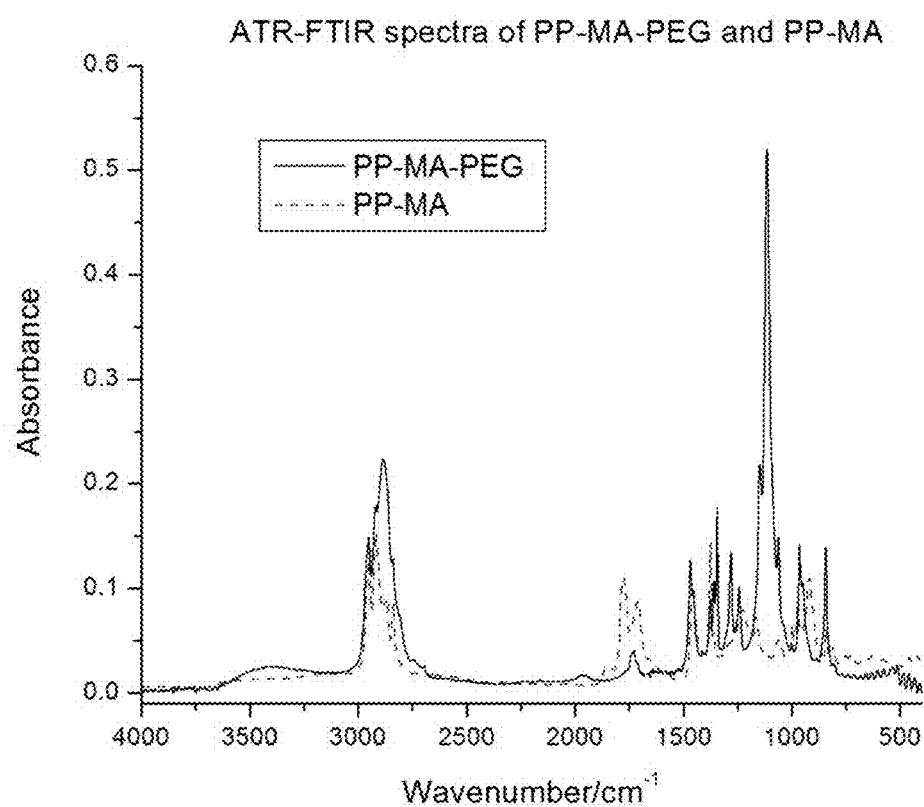
FIG. 5 is an ATR-FTIR spectrum of PEG-bearing maleated polypropylene (PP-MA-PEG) and maleated polypropylene (PP-MA).

FIG. 5 shows the ATR-FTIR spectrum of PP-MA-PEG sample. A strong peak emerged at 1115 cm$^{-1}$, corresponding to the C—O stretching mode due to the ether (—O—CH$_2$—) linkage in PEG. On the other hand, the band typical of the unreacted maleic anhydride groups that should appear at about 1780 and 1856 cm$^{-1}$ for symmetric and asymmetric >C=O frequency of the C=O groups on the cyclic anhydride structure, respectively disappeared on the ATR spectrum of PP-MA-PEG. The C=O band seen between 1725 cm$^{-1}$ and 1500 cm$^{-1}$ could represent the hydrolysed maleic anhydride groups. At least one hydroxyl end group of PEG was covalently grafted to the PP backbone by esterification through ring opening of the anhydride structure and this might result in a partially converted acid form of the maleic anhydride group. The result confirms that PEG was engrafted onto PP-MA backbone and a portion of PEG chain tended to migrate to the material surface.

2.2 Preparation of PP/PP-MA-PEG

A clear grade PP (Total Petrochemicals Lumicene® MR10MX0) in granular form was selected as the base plastic for preparation of antimicrobial PP resins. PP/PP-MA-PEG was prepared by extruding a dry mixture of the PP granules and PP-MA-PEG powders on a drum mixer by the same condition. In this case, 7.5 g of PP-MA-PEG was blended with 92.5 g PP to give a total 100 g of the mixture which was subsequently extruded on a single-screw extruder. The temperature settings were 180° C. and 185° C. for the barrel and the die of the extruder and the speed of the screw was 7 rpm for extrusion. The extrudate in the form of short filaments was cooled down in air and then cryogenically granulated into powders with a three-blade pulverizer.

Figure 6A:
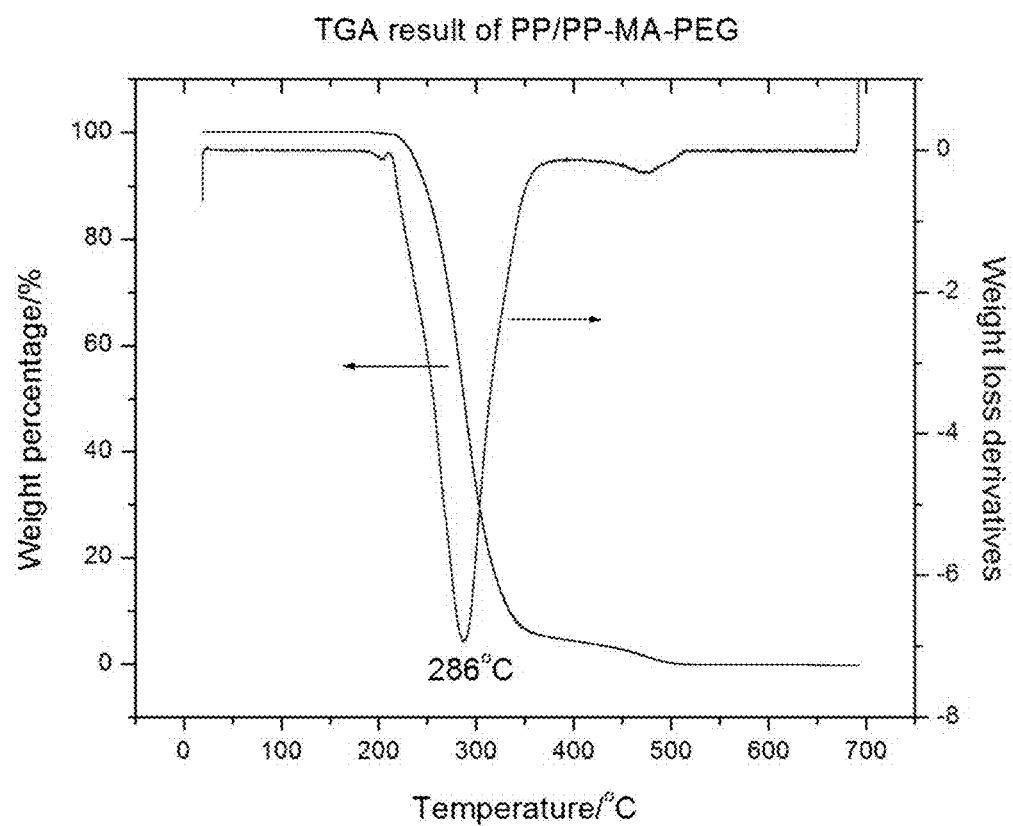
FIG. 6 is a TGA and DSC thermogram of an antimicrobial PP resin (PP/PP-MA-PEG) using PP-MA-PEG as masterbatch.
Figure 6B:
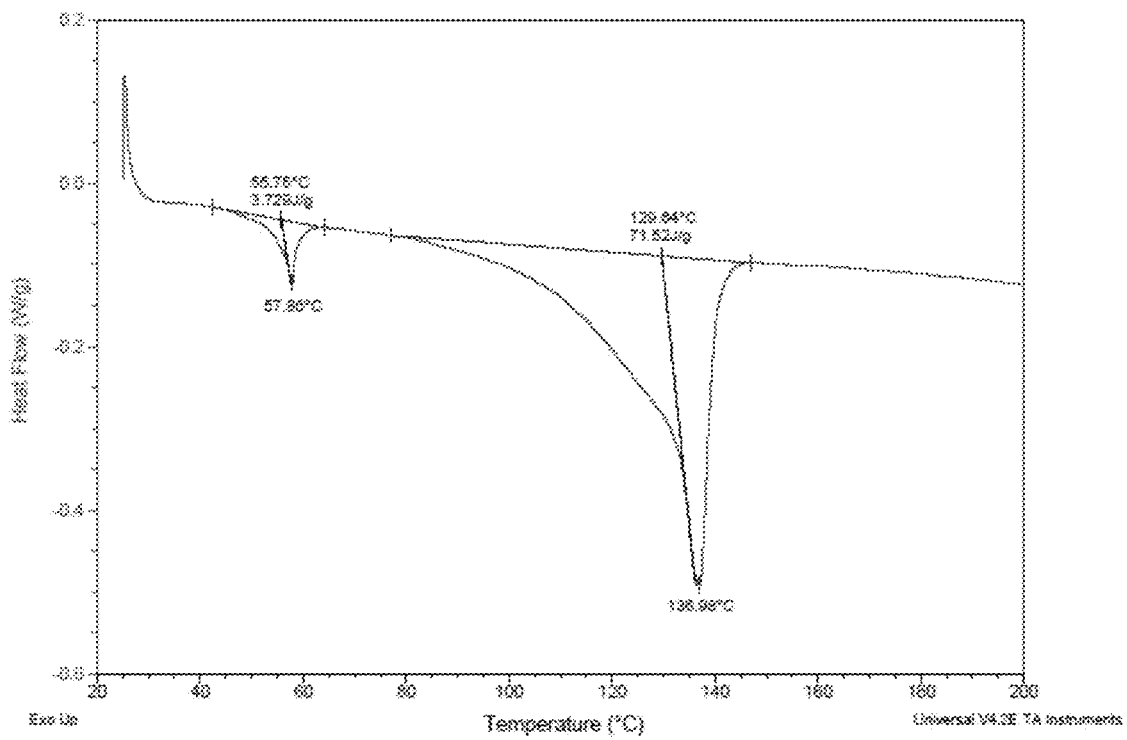
Figure 6B:
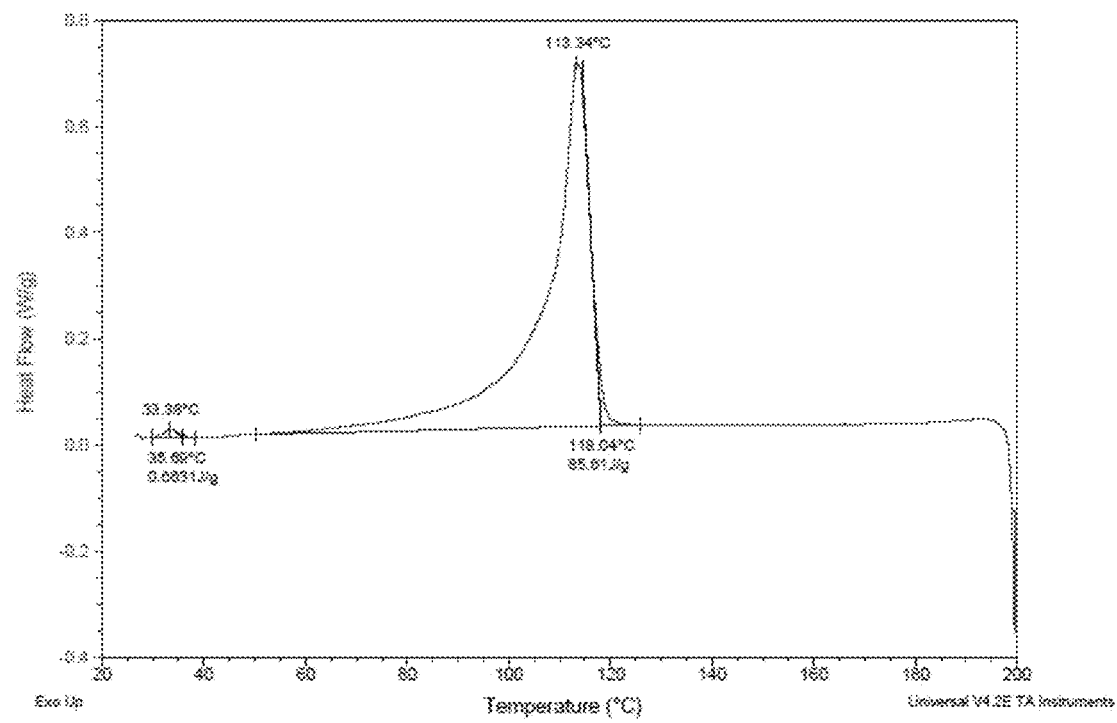

FIG. 6a shows the TGA weight loss curve of PP/PP-MA-PEG wherein the peak decomposition temperature approached to 300° C., a value higher than that of the base PP plastic (277° C.). FIG. 6b similarly indicates the formation of the phase separated morphology of the as-extruded PP/PP-MA-PEG resin by exhibiting two endothermic peaks centered at about 57 and 137° C. which were respectively characteristic of PEG and PP constituents.

Embodiment 3

3.1 Extrusion of PEG-Modified Maleated Olefin Bearing Polypropylene (PP/PP-MA-C/PEG) as Masterbatch PP/PP-MA-C/PEG was prepared by reactively extruding a dry blend mixture of three solid resin components: (1) PP (Total Petrochemicals Lumicene® MR10MX0), a random olefin copolymer; (2) PP-MA-C (Dow® Amplify™ GR 216), a maleic anhydride-grafted olefin plastomer and (3) PEG 10,000 (Tianjin Kermel). Prior to extrusion, 50 g of PEG 10,000 powders were pre-mixed together with 100 g of PP-MA-C pellets and 900 g of PP granules on the drum mixer. The dry blend mixture was fed into the twin-screw extruder from the front hopper. The barrel temperatures beginning from the front to the rear were 170° C., 180° C., 180° C., 180° C., 180° C., 180° C., 180° C. and 170° C. The feed frequency was 2 Hz while the speed of the screw was 150 rpm. The extrudate was cooled down in a water bath forming a solid filament and finally pelletized with a pelletizer. The pelletized resins were dried in a ventilated oven at 50° C. overnight.

Figure 7:
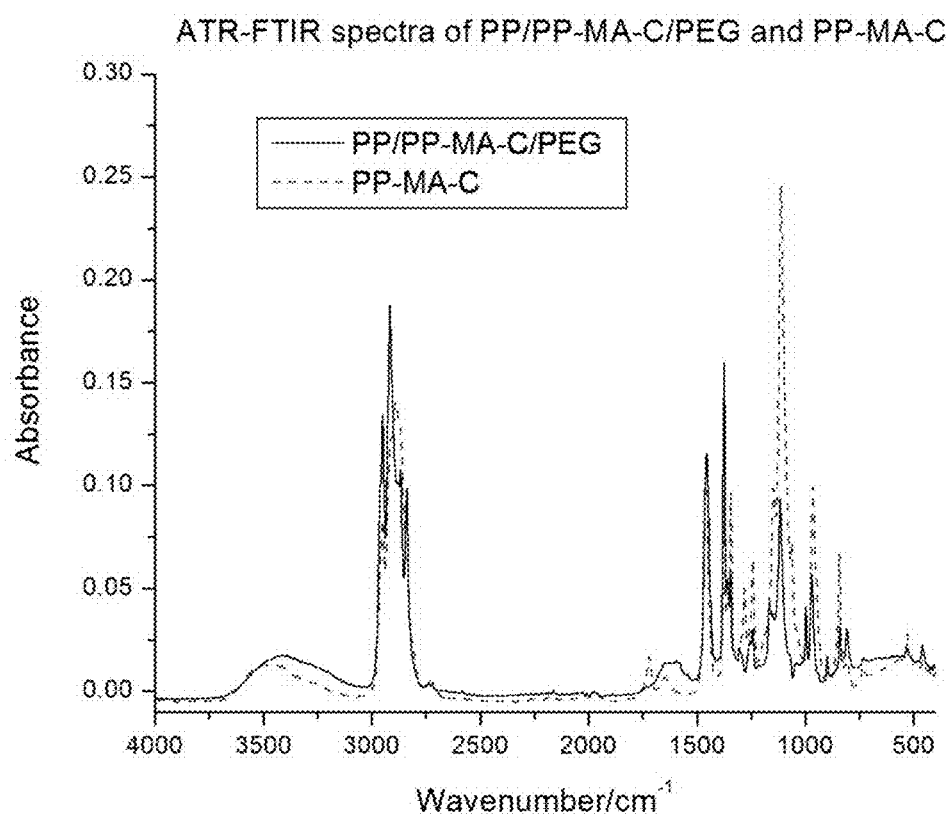
FIG. 7 is an ATR-FTIR spectrum of PEG-modified maleated olefin bearing polypropylene (PP/PP-MA-C/PEG) and maleated olefin bearing polypropylene (PP-MA-C).

FIG. 7 shows the ATR-FTIR spectrum of PP/PP-MA-C/PEG as compared with PP-MA-C. The melt flow index of PP/PP-MA-C/PEG was also measured to be 4.88 and 13.40 g/10 min respectively at 190 and 230° C. under the load of 2.16 kg, following the industrial standard of ASTM D1238-10. The results were higher than the values of 4.14 and 9.36 g/10 min recorded for the pristine PP (MR10MX0) under the same conditions. The increase of the melt flow index of PP after PEG modification is owing to the fact that PEG had a much lower melting point and molecular weight than PP. This result implicates that the PEG molecules tended to partition to melt surface during extrusion and therefore maintained the chance to reside PEG in the sample surface upon solidification.

Embodiment 4

4.1 Two-Step Fabrication of N-(4-hydroxyphenyl)maleimide-Modified PEG Bearing Polypropylene (PP/HPM-PEG) as Masterbatch HPM-PEG, as an antifouling masterbatch precursor, was synthesized according to Equations (3)-(5). N-(4-hydroxyphenyl)maleimide (HPM) was prepared by addition of maleic anhydride (1.67M) and 4-aminophenol (1.67M) in dimethylformamide (DMF) followed by intramolecular condensation via a highly hygroscopic phosphorus pentoxide reagent (0.33M) and concentrated sulphuric acid (0.42M) leading to a closed ring maleimide group in a one-pot reaction. Hydroxyl end groups of a PEG 10,000 (Tianjin Kermel) chain were subsequently activated by tosylation in a 1:5 molar ratio to tosyl chloride to generate PEG-OTs in the presence of a base catalyst, such as triethylamine (Et$_3$N, 0.25M in dichloromethane). 0.025 M PEG-OTs and HPM in a 1:1 molar ratio were reacted under reflux in acetone in the presence of excess triethylamine (20:1 with respect to HPM) for at least two days. p-toluenesulfonic acid which was one major by-product formed insoluble acid-base adducts with triethylamine and precipitated out from the reaction solution. Finally, the acetone solution was filtered to remove the adduct by-products and then subjected to precipitation to yield HPM-PEG as deep orange powders in diethyl ether in the second step of filtration.

Equation (3)-(5):

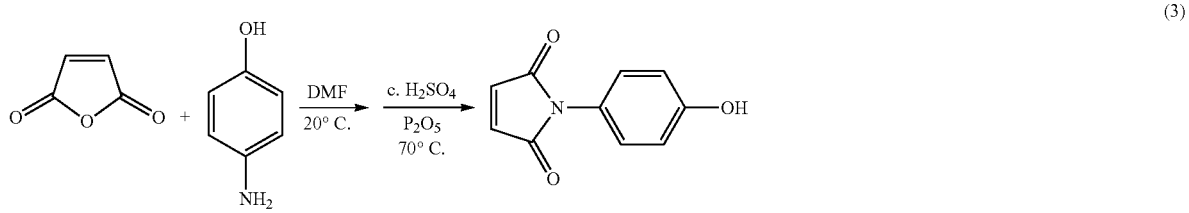

(3)

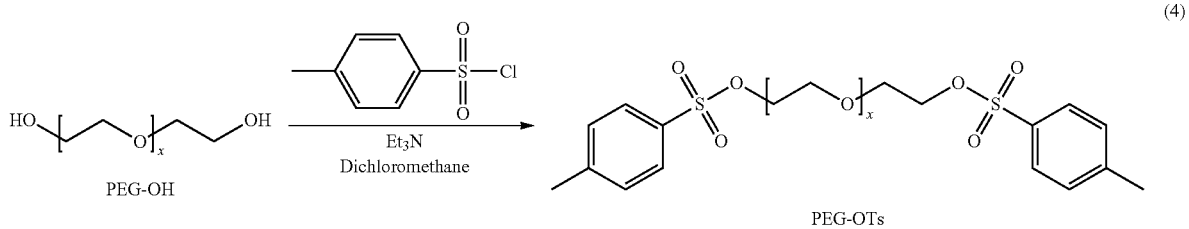

(4)

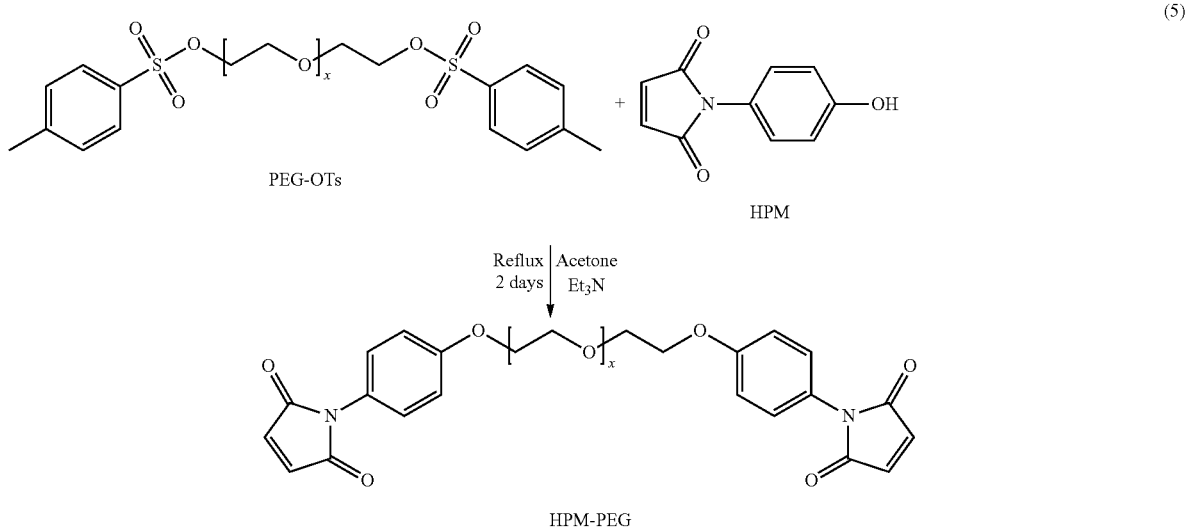

(5)

In the second step, prior to the extrusion process, 500 g PP (GD-150, Maoming Petro-Chemical Shihua Company), 2.5 g 2,5-bis(tert-butylperoxy)-2,5-dimethylhexane (Arkema Luperox® 101XL45), and 25 g HPM-PEG were pre-mixed on the rotating drum mixer by the same condition. Luperox® 101XL45, a heat-sensitive initiator, was added to generate free radicals by abstraction of hydrogen atoms from PP to allow additive coupling of PEG to PP via the maleimide group by extrusion. The reactive extrusion of the ternary blend was performed on the twin-screw extruder. The barrel temperature profile from the front to the rear was read as: 190° C., 200° C., 200° C., 200° C., 200° C., 190° C., 190° C., and 190° C. The feed frequency was 2 Hz and the speed of the screw was 150 rpm. The extrudate was solidified from melt upon cooling in water and finally subjected to pelletization. The plastic pellets were then dried in oven at 50° C. overnight to remove the absorbed moisture.

Figure 8:
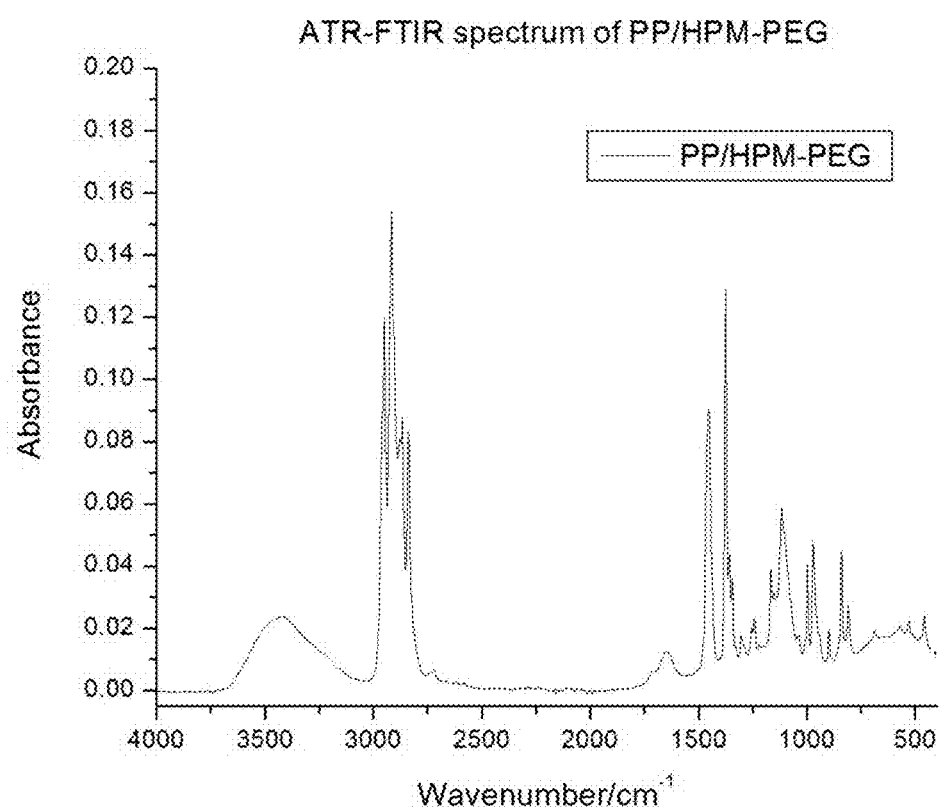
FIG. 8 is an ATR-FTIR spectrum of N-(4-hydroxyphenyl) maleimide-modified PEG bearing polypropylene (PP/HPM-PEG).

The melt flow index of the pristine PP (GD-150) was measured to be 9.68 and 43.6 g/10 min at 190° C. and 230° C. under the load of 2.16 kg. The melt flow index of PP/HPM-PEG resin was however not measureable even at 190° C. due to extremely high fluidity under the same load condition. The increase in melt flow index of the resin helps solve the mold filling problem by increasing the injection speed rather than increasing the processing temperature. A higher melt flow is recommended for injection molding in particular for thin-walled applications owing to the prerequisite of high shear rates being encountered. FIG. 8 is an ATR-FTIR spectrum of N-(4-hydroxyphenyl)maleimide-modified PEG bearing polypropylene (PP/HPM-PEG).

5.1 Bacterial Adsorption Studies on Antimicrobial Thermoplastic Resins and Masterbatches Thereof Test specimens in circular discs with diameter and thickness of 64 mm and about 1 mm respectively were prepared by melting and fusion of the solid resin samples in a glass Petri dish on a heating plate. Solidification was done by cooling in atmospheric pressure at room temperature. To examine the bacterial adhesion and growth behavior on these pristine or modified specimen surfaces after thermoforming, swab test was achieved by collecting the adherent bacteria from the specimen surface using a cotton tip applicator (Medicom) prior to incubation with inoculums for the time elapsed for bioburden challenge test. Originally, plate counting of colonies along with serial dilution (in case of obtaining large colony populations) is used to determine the amount of viable bacteria in the inoculums after contact with products for a designated time at a given temperature. Slight modification on the protocol was made for executing the bacterial adsorption studies involving swabs. The tests were based on the original culture methodology but the amount of bacteria being attached to the product surface after contact was determined to assess the bacteria repellent performance of the plastic samples and their resistance towards bacterial colonization. In brief, a test inoculum of a selected *Escherichia coli* strain (ATCC® 8739™) was prepared and enumerated upon incubation according to the Japanese industrial standard (JIS Z 2801:2000) by finally adjusting the $OD_{600}$ of inoculum to 0.5 determined with a microplate reader (Molecular Devices SpectraMax M3). This corresponds to a population of approximately $10^8$ bacteria counts per millimeter of a 1/500 nutrient broth medium. Bioburden challenge procedure was subsequently carried out by incubating the inoculum of *Escherichia coli* (3 ml) over one face of a thermoformed plastic disc sample at 37° C. for 24 hours, followed by rinsing with 0.9% w/v saline for two to three times. The adherent bacteria remaining on the rinsed sample surfaces, which were inclined to biofilm growth, were swabbed and then dislodged to 1 millimeter of 0.9% w/v saline on a vortexer to perform conventional spread plating.

Figure 9:
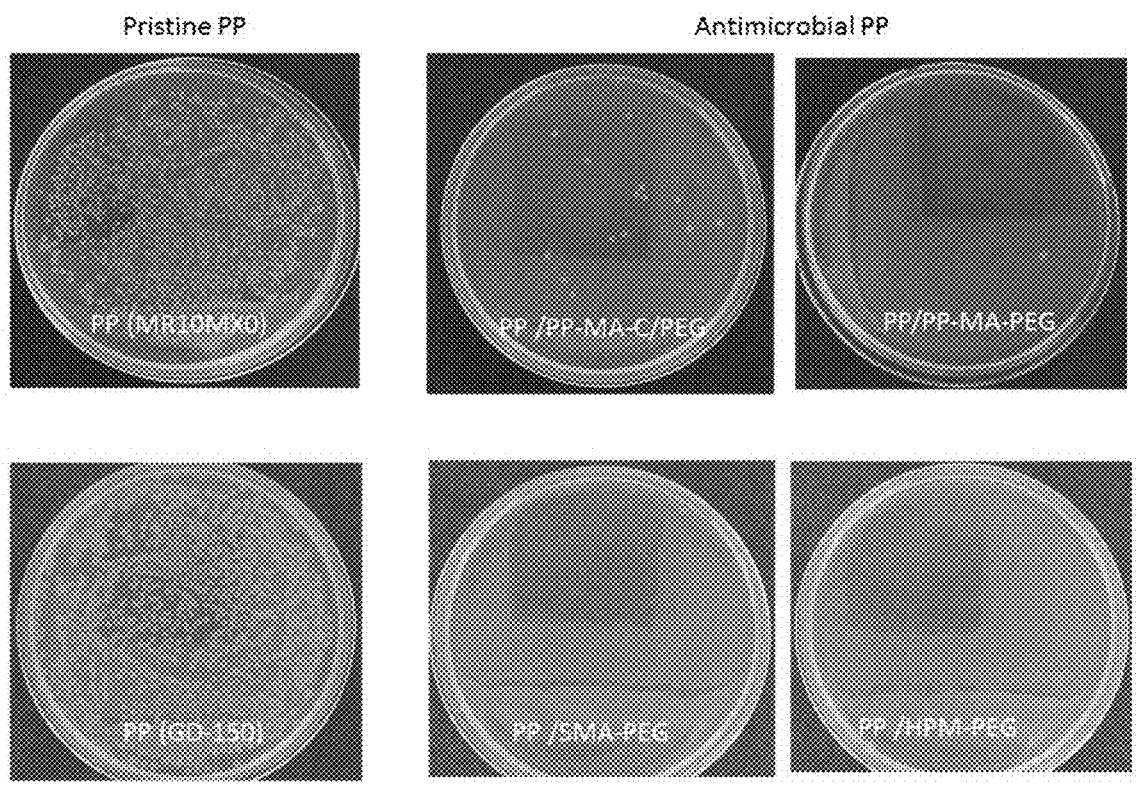
FIG. 9 is a representative plate count result (100× dilution) of *Escherichia coli* adsorption on specimens thermoformed from antimicrobial PP resin.
Figure 10:
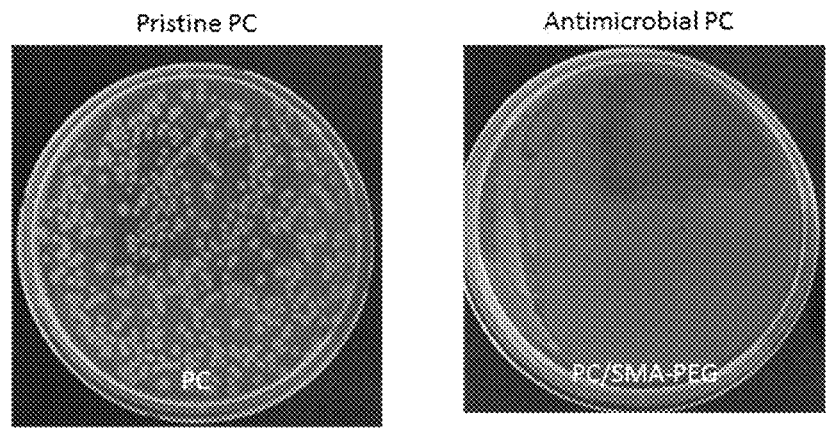
FIG. 10 is a representative plate count result (100× dilution) of *Escherichia coli* adsorption on specimens thermoformed from antimicrobial PC resin.

FIGS. 9 and 10 show the *Escherichia coli* colonies developed from the adherent species collected from several examples of antimicrobial masterbatches and resins deriving from PP and PC as the base plastics respectively: PP/PP-MA-C/PEG, PP/HPM-PEG, PP/SMA-PEG, PP/PP-MA-PEG and PC/SMA-PEG in comparison with their respective controls (pristine base plastics) without treatment. The bacterial adsorption studies were repeated once by using two separate test specimens for each sample. The complete set of spread count data is compiled in Table 1 which indicates that PP and PC after modifications with PEG-derived compounds or masterbatches by different methods demonstrated notable improvement of resistance towards *Escherichia coli* adsorption onto the sample surfaces.

Table 1 is a summary of plate count results of *Escherichia coli* adsorption on thermoformed specimens.

| | Samples | Dilution (Colony Forming Unit) | | |
| --- | --- | --- | --- | --- |
| | | 10x | 100x | 1000x |
| Resins with low processing temperature | PP(MR10MX0) #1 | >300 | >300 | 41 |
| | PP(MR10MX0) #2 | >300 | >300 | 46 |
| | PP/PP-MA-C/PEG #1 | 148 | 15 | 1 |
| | PP/PP-MA-C/PEG #2 | >300 | 65 | 4 |
| | PP/PP-MA-PEG #1 | 15 | 1 | 0 |
| | PP/PP-MA-PEG #2 | 0 | 0 | 0 |
| | PP(GD-150) #1 | >300 | >300 | 34 |
| | PP(GD-150) #2 | >300 | >300 | 44 |
| | PP/SMA-PEG #1 | 0 | 0 | 0 |
| | PP/SMA-PEG #2 | 0 | 0 | 0 |
| | PP/HPM-PEG #1 | 0 | 0 | 0 |
| | PP/HPM-PEG #2 | 0 | 0 | 0 |
| Resins with high processing temperature | PC #1 | >300 | >300 | >300 |
| | PC #2 | >300 | >300 | 197 |
| | PC/SMA-PEG #1 | 10 | 0 | 0 |
| | PC/SMA-PEG #2 | 12 | 0 | 0 |

5.2 Bacterial Adsorption Studies on Specimens Injection-Molded from Antimicrobial PE Resins (PE/SMA-PEG)

The pristine PE and PE/SMA-PEG resins were injection-molded into plastic circular dishes with a diameter and height of 50 mm and 15 mm respectively via a desktop vertical plunger-type injection molding machine (Model AB-400M, A.B.Machinery, Canada). The barrel temperature was 200° C. The pressure was 60 psi.

The bacterial adsorption studies were performed to directly observe the *Escherichia coli* attached on the surface of the sample.

Figure 11:
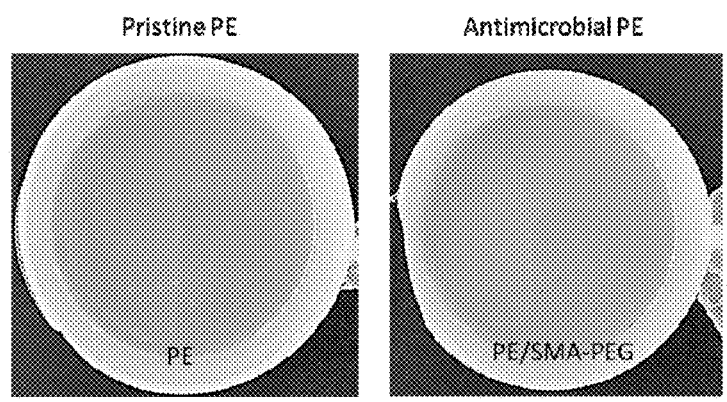
FIG. 11 is a representative *Escherichia coli* adsorption test result on specimens injection-molded from antimicrobial PE resin.

10 mL of diluted *Escherichia coli* suspension in 1/500 nutrient broth medium with a cell density of approximately $10^4$ cells/mL was added into the injection-molded plastic dishes injection-molded from PE/SMA-PEG. The dishes were directly incubated against the bacterial suspension at 37° C. for 24 hours, followed by rinsing with 0.9% w/v saline for two to three times. 6 mL of nutrient agar solution at about 50° C. was poured to the dishes and further incubated overnight at 37° C. The agar solution gradually solidified as nutrient source and those viable bacteria which had adhered strongly to the dish surface developed into colonies at the bottom of the plastic dishes. FIG. 11 demonstrates the development of colonies between PE/SMA-PEG and the pristine PE without treatment. Colonies developed only on the dish injection-molded from the pristine PE meaning that the specimens injection-molded from PE/SMA-PEG resins was able to prevent initial inhabitation of bacteria.

What is claimed is:

1. An antimicrobial thermoplastic resin, comprising a masterbatch and a basic plastic selected from the group consisting of a polyolefin and a polycarbonate; wherein the masterbatch comprises an antifouling reagent attached to a base polymer backbone via a reactive linker; wherein the antifouling reagent comprises a polyethylene glycol (PEG); the reactive linker is maleic anhydride or a maleimide; and the antimicrobial thermoplastic resin is biocide-free, has bacterial-repellent properties and is prepared by melt extrusion of the masterbatch and the basic plastic, wherein the masterbatch comprises a co-polymer comprising a polystyrene repeating unit and a repeating unit represented by:

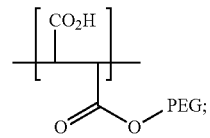

a co-polymer comprising a polypropylene repeating unit and a repeating unit represented by:

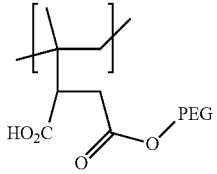

a polymer comprising a polypropylene repeating unit crosslinked with an agent represented by:

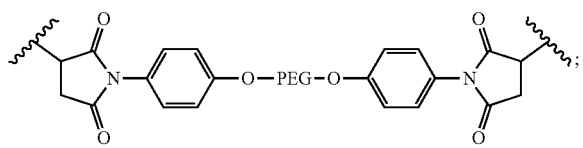

or a co-polymer comprising a polypropylene repeating unit and a repeating unit prepared by the reaction of a maleic anhydride-grafted olefin plastomer and polyethylene.

2. The antimicrobial thermoplastic resin of claim 1, wherein the basic plastic is a thermoplastic and melt-processable plastic resin selected from a group consisting of polyethylene, polypropylene, and polycarbonate.

3. The antimicrobial thermoplastic resin of claim 1, wherein the antifouling reagent is biocompatible.

4. The antimicrobial thermoplastic resin of claim 1, further comprising non-biocidal additives selected from a group consisting of catalysts, initiators, stabilizers, foaming agents, plasticizers, thickeners, lubricants, fillers, impact modifiers, anti-blocks, clarifiers, antistatics, flame retardants and/or colorants.

5. The antimicrobial thermoplastic resin of claim 1, wherein the antimicrobial thermoplastic resin is thermally processable to 350° C.

6. The antimicrobial thermoplastic resin of claim 1, wherein the masterbatch is prepared by wet chemistry method.

7. The antimicrobial thermoplastic resin of claim 1, wherein the masterbatch is present at a concentration of 4.7% to 7.5% (m/m) in the antimicrobial thermoplastic resin.

8. The antimicrobial thermoplastic resin of claim 7, wherein the basic plastic is polyethylene, polypropylene, or polycarbonate.

9. A method for preparing the antimicrobial thermoplastic resin of claim 1, comprising the steps of:

attaching an antifouling reagent to a base polymer via a reactive linker thereby forming a masterbatch, wherein the antifouling reagent comprises a polyethylene glycol (PEG);

and reactive linker is maleic anhydride or a maleimide;

drying the masterbatch;

pelletizing the masterbatch;

melt extruding the masterbatch and a basic plastic selected from the group consisting of a polyolefin and a polycarbonate to prepare an antimicrobial thermoplastic resin; and molding the antimicrobial thermoplastic resin into a finished article through a thermoforming process.

10. The method of claim 9, wherein the thermoforming process is selected from a group consisting of spinning, extrusion, injection, compression, foaming and drawing.

11. The method of claim 10, wherein the finished article is in a form selected from a group of solid, monolith, tube, composite, fiber, film, sheet and varnish.

12. The method of claim 9, wherein the basic plastic is a thermoplastic and melt-processable plastic resin selected from a group consisting of polycarbonate, polyethylene, and polypropylene.

13. The method of claim 9, wherein the step of attaching the antifouling reagent to the base polymer via a reactive linker thereby forming a masterbatch is performed by a wet chemistry method.

* * * * *